United States Patent [19]

Ikariya et al.

[11] Patent Number: 4,678,856
[45] Date of Patent: Jul. 7, 1987

[54] METHOD OF MANUFACTURING AROMATIC URETHANE AND INTERMEDIATE PRODUCT THEREOF

[75] Inventors: Takao Ikariya, Tokyo; Masanori Itagaki, Yokohama; Masatsugu Mizuguchi, Kawasaki; Itaru Sakai, Yokohama; Osamu Tajima, Kamakura, all of Japan

[73] Assignee: Nippon Kokan Kabushiki Kaisha, Tokyo, Japan

[21] Appl. No.: 902,527

[22] Filed: Sep. 2, 1986

[30] Foreign Application Priority Data

| Sep. 4, 1985 | [JP] | Japan | 60-195306 |
| Sep. 4, 1985 | [JP] | Japan | 60-195307 |
| Sep. 4, 1985 | [JP] | Japan | 60-195308 |
| Nov. 8, 1985 | [JP] | Japan | 60-250497 |
| Nov. 8, 1985 | [JP] | Japan | 60-250499 |

[51] Int. Cl.$^4$ .............. C07C 125/065; C07C 125/067; C07C 125/073; C07C 125/075
[52] U.S. Cl. .................. 560/24; 546/308; 546/309; 560/12; 560/25; 560/27; 560/28; 560/30; 560/31; 560/32; 564/48; 564/55
[58] Field of Search .......... 564/55, 48; 560/24, 560/25, 12, 30, 31, 32, 27, 28; 546/308, 309

[56] References Cited

U.S. PATENT DOCUMENTS

| 2,871,259 | 1/1959 | Levy | 560/24 X |
| 4,178,455 | 12/1979 | Hirai et al. | 560/24 |
| 4,491,670 | 1/1985 | Bhaduri et al. | 560/24 |
| 4,603,216 | 7/1986 | Grate et al. | 560/24 |

Primary Examiner—Bernard Helfin
Attorney, Agent, or Firm—Frishauf, Holtz, Goodman & Woodward

[57] ABSTRACT

The present invention relates to a method of manufacturing aromatic urethane, an aromatic mononitro-compound, an aromatic primary amine, and carbon monoxide being reacted using a catalyst containing a platinum group metal-containing compound as a major constituent to prepare N,N'-di-substituted urea. The resultant N,N'-di-substituted urea is reacted with a hydroxyl group-containing organic compound to prepare an aromatic primary amine and aromatic urethane, and the aromatic primary amine is separated to obtain aromatic urethane.

9 Claims, No Drawings

METHOD OF MANUFACTURING AROMATIC URETHANE AND INTERMEDIATE PRODUCT THEREOF

BACKGROUND OF THE INVENTION

1. Field of the Invention

The present invention relates to a method of manufacturing aromatic urethane.

2. Description of the Prior Art

Various conventional methods of manufacturing aromatic urethane have been proposed. These methods are classified into a method using an aromatic nitro-compound as a starting material and a method using an aromatic primary amine as a starting material.

According to the conventional method using an aromatic nitro-compound as a starting material, an aromatic nitro-compound (e.g., nitrobenzene), an organic compound (e.g., an alcohol) containing a hydroxyl group, and carbon monoxide are allowed to react reductively with each other in the presence of a catalyst having a platinum group compound such as a palladium or rhodium compound as a major constituent to manufacture aromatic urethane. Examples of this method are described in Japanese Patent Disclosure (Kokai) Nos. 51-98240 and 54-22339 and Japanese Patent Publication No. 43-23939.

According to the conventional method using an aromatic primary amine as a starting material, aromatic primary amine (e.g., aniline), an organic compound (e.g., an alcohol) containing a hydroxyl group, and carbon monoxide are allowed to react oxidatively with each other in the presence of an oxidizer such as oxygen or an organic nitro-compound through a catalyst containing a platinum group metal compound such as a palladium or rhodium compound to prepare aromatic urethane. Examples of this method are described, e.g., in Japanese Patent Disclosure (Kokai) Nos. 55-124750, 55-120551, and 59-172451.

In either method, since use of only a platinum group metal compound as the major constituent of the catalyst results in low synthetic activity of urethane, a halogen compound such as iron chloride, iron oxychloride, vanadium oxychloride, or potassium iodide is used as an assistant catalyst. A mixture of the platinum group metal compound and the assistant catalyst are dissolved in a reacting system. However, the halogen compound greatly corrodes a metal material such as a reaction chamber and piping valves. For this reason, an expensive metal material having a good anticorrosion property must be used.

When a platinum group metal compound as a main catalyst is dissolved in a reaction solution or a solid platinum group metal compound is used, the platinum group metal partially contains a halogen compound and the halogen compound is eluted in the reaction solution. In order to recover the platinum group metal compound from the reaction solution at the end of reaction, cumbersome operations and high cost are required.

In addition, an organic compound containing a hydroxyl group for a reaction material is used as a reaction solution, and aromatic urethane has high solubility in the organic compound containing a hydroxyl group. For this reason, in order to crystallize and separate aromatic urethane from the solution after reaction, the solution must be cooled to an extremely low temperature of several tens of minus degrees in centigrade. Alternatively, the solution must be condensed and cooled to allow precipitation of crystals. Even if such precipitation is performed, it is difficult to recover aromatic urethane dissolved in the solution separately from the catalyst. Another method of recovering aromatic urethane is a distillation method. In this case, however, since the dissolved catalyst must be recovered as a distillation residue, aromatic urethane must be distilled. However, aromatic urethane is a compound having a high boiling point and must be distilled at a temperature of 100° to 150° C. under a high vacuum of about 1 mmHg.

Furthermore, if an aromatic nitro-compound is used as a starting material, a small amount of nonreacted aromatic nitro-compound is left in the reaction solution. If distillation is performed in this state, aromatic urethane is colored in brown by the aromatic nitro-compound.

As described above, it is difficult to separate and recover aromatic urethane from the solution and further recover the catalyst for reuse regardless of a recovery method, i.e., crystallization or distillation.

If an aromatic nitro-compound is used as a starting material an aromatic amine is by-produced, and if an aromatic primary amine is used as a starting material, N,N'-di-substituted urea is by-produced, thereby decreasing the yield of aromatic urethane.

SUMMARY OF THE INVENTION

It is an object of the present invention to provide a method of manufacturing aromatic urethane to solve various conventional problems without using a halogen compound as an assistant catalyst, to prepare aromatic urethane according to a two-step reaction, to increase the yield of intermediate product and aromatic urethane and to easily recover the catalyst and the resultant aromatic urethane.

In order to achieve the above object of the present invention, there is provided a method of manufacturing aromatic urethane, comprising:
the urea producing step of reacting an aromatic mononitro-compound, an aromatic primary amine, and carbon monoxide by using a catalyst having a platinum group metal-containing compound as a major constituent to prepare N,N'-di-substituted urea and of separating and recovering the resultant N,N'-di-substituted urea from a reaction solution;
the step of reacting the N,N'-di-substituted urea as an intermediate product prepared in the urea producing step with an organic compound containing a hydroxyl group to prepare an aromatic primary amine and aromatic urethane, and of separating the aromatic primary amine from the aromatic urethane, thereby obtaining the aromatic urethane; and
the step of recirculating the separated aromatic primary amine in the urea producing step.

DETAILED DESCRIPTION OF THE PREFERRED EMBODIMENT

An aromatic mononitro-compound, aromatic primary amine, and carbon monoxide are reacted using a catalyst using a ruthenium complex compound as a major constituent.

This reaction progresses according to the following general formula:

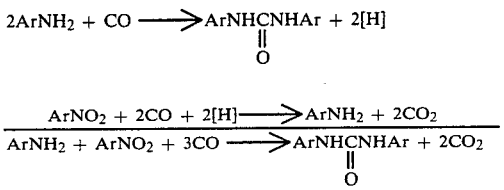

The aromatic primary amine comprises anilines, aminonaphthalenes, aminoanthracenes, amonobiphenyls, and the like. Examples of these aromatic primary amine are aniline, o-, m- and p-toluidine, o-, m- and p-chloroaniline, α- and β-naphthylamine 2-methyl-1-aminonaphthalene, diaminobenzene, triaminobenzene, aminotoluene, diaminotoluene, aminopyridine, diaminopyridine, aminonaphthalene, diaminonaphthalene, an isomer thereof, and a mixture thereof.

An aromatic mononitro-compound comprises nitrobenzenes, nitronaphthalenes, nitroanthracenes, nitrobiphenyls, and a nitro-compound wherein at least one hydrogen atom is substituted with another substituent (e.g., a halogen atom, a cyano group, an alicyclic group, an aromatic group, an alkyl group, an alkoxyl group, a sulfoxide group, a sulfone group, a carbonyl group, an ester group, and an amide group). Examples of these aromatic mononitro-compound are nitrobenzene, o-, m-, and p-nitrotoluene, o-nitro-p-xylene, 2-methyl-1-nitronaphthalene, o-, m- and p-chloronitrobenzene, 1-bromo-4-nitrobenzene, an isomer thereof, and a mixture thereof. It should be noted that a nitro-compound corresponding to the selected aromatic primary amine is preferable.

Carbon monoxide may be pure carbon monoxide, or may be mixed with nitrogen, argon, helium, carbon dioxide gas, hydrocarbon, or halogenated hydrocarbon.

A platinum group metal-containing compound is a compound of a platinum group metal (e.g., ruthenium, rhodium, palladium, and platinum) and an organometallic compound having a ligand (e.g., carbon monoxide and a phosphine) or an organic group). In this case, the platinum group metal-containing compound preferably does not contain a halogen atom. Preferred examples of such a compound are a ruthenium complex compound such as $Ru_3(CO)_{12}$, $H_4Ru_4(CO)_{12}$, $Ru(CO)_3(PPh_3)_2$, $Ru(CO)_3(dppe)$, $(Ru(CO)_2(HCO)_2P(C-C_6H_{11})_3)_2$, and $Ru(acac)_3$, and a rhodium complex compound such as $Rh_6(CO)_{16}$, $RhH(CO)(PPh_3)_3$, $Rh(acac)(CO)(PPh_3)$, $Rh(acac)(CO)_2$, and $Rh(acac)_3$, wherein dppe represents diphenylphosphinoethane and acac represents acetylacetonato.

Cobalt, iron, rhodium, palladium, or the like is combined with a platinum group metal compound.

When a ruthenium complex compound is used as a major constituent of a catalyst, a reaction temperature generally falls within the range of 30° to 300° C. and preferably 120° to 200° C. A reaction pressure generally falls within the range of 1 to 500 kg/cm² and preferably 10 to 300 kg/cm².

When a rhodium complex compound is used as a major constituent of a catalyst, a reastion temperature generally falls within the range of 80° to 300° C. and preferably 120° to 200° C.

A reaction pressure generally falls with the range of 1 to 500 kg/cm² and preferably 20 to 300 kg/cm². The reaction time varies according to other conditions but generally falls within the range of 0.5 to 24 hours.

The reaction can be achieved without using a solvent. However, a proper solvent such as an aromatic hydrocarbon (e.g., benzene, toluene, xylene, and cyclohexane) may be used. When the concentration of aromatic primary amine as a starting material is increased, the reaction rate is increased. Therefore, an aromatic primary amine is used in an excessive amount and can be substantially used as a solvent, thereby achieving the reaction at a maximum rate.

The resultant N,N'-di-substituted urea has low solubility with respect to the solvent. For this reason, the solution after the reaction is simply cooled to precipitate N,N'-di-substituted urea as crystals. Therefore, the resultant solution is filtered to obtain solid N,N'-di-substituted urea. The catalyst is obtained as a solution together with the solvent. The solvent containing the catalyst can be used again.

The organic compound containing N,N'-di-substituted urea and a hydroxyl group reacts according to the following formula to prepare aromatic primary amine and aromatic urethane.

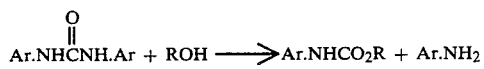

The organic compound containing a hydroxyl group comprises monoalcohols and monophenols. Examples of such a compound are monoalcohols (e.g., methyl, ethyl, n-propyl, isopropyl, n-butyl, isobutyl, and t-butyl) and alkyl phenols (e.g., phenol, chlorophenol, and methyl, ethyl, n-propyl, and isopropyl substituted phenol).

The reaction temperature generally falls within the range of 80° to 300° C. and preferably 120° to 200° C. The reaction pressure is a pressure naturally obtained at a reaction temperature of the hydroxyl group-containing organic compound or solvent.

The reaction time varies according to other conditions but generally falls within the range of 1 to 10 hours.

This reaction can be achieved without using a catalyst.

After the end of reaction, distillation is performed to recover aromatic urethane as a distillation residue. On the other hand, aromatic primary amine is recovered by distillation. Aromatic primary amine is used again in the production of N,N'-di-substituted urea in the first-step reaction.

According to the present invention, since N,N'-di-substituted urea produced in the first-step reaction has low solubility in the solvent, it can be easily crystallized, and N,N'-di-substituted urea can be effectively recovered by filtration. In addition, the catalyst is contained together with the solvent in the filtered solution. The catalyst can be reused in the first-step reaction.

The catalyst contains a compound containing a platinum group metal as a major constituent. A halogen compound need not be used. For this reason, the metal members required for the reaction are little corroded, and an expensive material need not be used.

The first-step reaction is free from a side reaction and can produce N,N'-di-substituted urea at a high yield.

An excessive amount of aromatic primary amine is added in the urea production reaction, and aromatic primary amine is used as a solvent to increase the reaction rate.

In the second-step reaction, the catalyst need not be used. Aromatic urethane is not eluted and can be recovered as a distillation residue. Aromatic primary amine as a distilled material and the compound containing a residual hydroxyl group have relatively low boiling points. Therefore, distillation can be performed at moderate conditions, thus simplifying the operations. In addition, the recovered aromatic primary amine can be reused in the first-step reaction. The second-step reaction results in little side reaction in the same manner as in the first-step reaction. Therefore, aromatic urethane can be prepared in the two-step reaction at a high yield.

EXAMPLES

The present invention will be described in detail by way of examples. In the following examples, term "alkyl carbamate" is used instead of term "urethane", and the individual material names are indicated.

EXAMPLE 1

3.82 g of nitrobenzene, 2.85 g of aniline, 34.58 g of toluene, and 0.10 g of $Ru_3(CO)_{12}$ were charged in an electromagnetic stirring type autoclave having an inner volume of 200 ml. Carbon monoxide was supplied to the autoclave at a pressure of 50 kg/cm$^2$. The materials were stirred and reacted at a temperature of 160° C. for 6 hours. After the reaction, the mixture was cooled to room temperature. The autoclave was then evacuated, and the reaction solution was filtered to obtain 5.91 g of crystals. The crystals were analyzed by liquid chromatography and found to have a 90% yield of N,N'-diphenyl urea for nitrobenzene. In addition, the reactive filtered solution containing the catalyst after the separation of N,N'-diphenyl urea was used to repeat the above test under identical conditions. The yield of N,N'-diphenyl urea was 90%.

3.00 g of the resultant crystals and 50.00 g of methyl alcohol were filled in another electromagnetic stirring type autoclave having an inner volume of 200 ml and were stirred and reacted at a temperature of 160° C. for 3 hours. When the reacted solution was analyzed, it had a 94% yield for N-phenylmethyl carbamate and a 95% yield for aniline.

EXAMPLE 2

Following the same procedures as in Example 1 except that 0.13 g of $Ru_3(CO)_{12}$ was used as the catalyst, nitrobenzene, aniline and carbon monoxide were reacted to prepare 5.94 g of N,N'-diphenyl urea crystals. The yield of N,N'-diphenyl urea for nitrobenzene was 94%.

Following the same procedures as in Example 1, 3.00 g of the crystals and 50.00 g of ethyl alcohol were reacted to obtain a 93% yield for N-phenylethyl carbamate and a 95% yield for aniline.

EXAMPLE 3

Following the same procedures as in Example 1 except that 0.31 g of $Ru(CO)_3(PPh_3)_2$ was used in place of $Ru_3(CO)_{12}$ as the catalyst, nitrobenzene, aniline and carbon monoxide were reacted to prepare 5.77 g of N,N'-diphenyl urea crystal. The yield of N,N'-diphenyl urea for nitrobenzene was 90%.

Following the same procedures as in Example 1, 3.00 g of the crystals and 50.00 g of ethyl alcohol were reacted to obtain a 92% yield for N-phenylmethyl carbamate and a 93% yield for aniline.

EXAMPLE 4

Following the same procedures as in Example 1 except that 0.31 g of $Ru(acac)_3$ was used in place of $Ru_3(CO)_{12}$ as the catalyst nitrobenzene and that the reaction time was 8 hours, aniline and carbon monoxide were reacted to prepare 6.04 g of N,N'-diphenyl urea crystals. The yield of N,N'-diphenyl urea for nitrobenzene was 96%.

Following the same procedures as in Example 1, 3.00 g of the crystals and 30.00 g of methyl alcohol were reacted to obtain a 93% yield for N-phenylmethyl carbamate and a 92% yield for aniline.

EXAMPLE 5

3.77 g of nitrobenzene, 2.78 g of aniline, 34.03 g of toluene, 0.38 g of $Rh_6(CO)_{16}$, and 1.24 g of triphenylphosphine were charged in an electromagentic stirring type autoclave having an inner volume of 200 ml. Carbon monoxide was supplied to the autoclave at a pressure of 50 kg/cm$^2$. The materials were stirred and reacted at a temperature of 160° C. for 9 hours. After the reaction, the mixture was cooled to room temperature. The autoclave was then evacuated, and the reaction solution was filtered to obtain 6.05 g of crystals. The crystals were analyzed by liquid chromatography and found to have a 93% yield for N,N'-diphenyl urea based on nitrobenzene.

3.00 g of the resultant crystals and 50.00 g of methyl alcohol were filled in another electromagnetic stirring type autoclave having an inner volume of 200 ml and were stirred and reacted at a temperature of 160° C. for 3 hours. When the reaction mixture was analyzed, it had a 93% yield for N-phenylmethyl carbamate and a 94% yield for aniline.

EXAMPLE 6

Following the same procedures as in Example 5 except that 0.39 g of $Rh_4(CO)_{12}$ was used as the catalyst nitrobenzene and the reaction time was 10 hours, nitrobenzene, aniline and carbon monoxide were reacted to prepare 5.76 g of N,N'-diphenyl urea crystals. The yield of N,N'-diphenyl urea based on nitrobenzene was 95%.

Following the same procedures as in Example 5, 3.00 g of the crystals and 50.00 g of ethyl alcohol were reacted to obtain a 93% yield for N-phenylethyl carbamate and a 95% yield for aniline.

EXAMPLE 7

Following the same procedures as in Example 5 except that 0.38 g of $Rh_6(CO)_{16}$ was used as the catalyst and triphenylphosphine was not added, nitrobenzene, aniline and carbon monoxide were reacted to prepare 1.16 g of N,N'-diphenyl urea crystals. The resultant crystals and the solution were analyzed to obtain a nitro benzene conversion of 20% and a 93% selectivity for converted nitrobenzene.

Following the same procedures as in Example 5, 1.00 g of the crystals and 20.00 g of methyl alcohol were reacted to obtain a 92% yield for N-phenylmethyl carbamate and a 93% yield for aniline.

EXAMPLE 8

3.71 g of nitrobenzene, 40.0 ml of aniline, and 0.0509 g of $Ru_3(CO)_{12}$ were charged in an electromagnetic stirring type autoclave having an inner volume of 200 ml. Carbon monoxide was supplied to the autoclave at a pressure of 50 kg/cm$^2$. The materials were stirred and reacted at a temperature of 160° C. for 1.5 hours. After the reaction, the mixture was cooled to room temperature. The autoclave was then evacuated, and the reaction solution was filtered to obtain 5.42 g of crystals. The filtered solution was analyzed by liquid chromatography and found to contain 0.37 g of N,N'-diphenyl urea. However, no nitrobenzene was detected.

The yield of N,N'-diphenyl urea separated from the solution was 85%. If N,N'-diphenyl urea contained in the solution was included, a total yield thereof was 91%. A turn over rate of the catalyst was 84 (mol-PhNo$_2$/mol-Ru.hr).

3.00 g of the singly separated N,N'-diphenyl urea and 50.00 g of methyl alcohol were filled in another electromagnetic stirring autoclave having an inner volume of 200 ml and were stirred and reacted at a temperature of 160° C. for 3 hours. After the reaction, the solution was analyzed to result in a 94% yield for N-phenylmethyl carbamate and a 95% yield for aniline.

EXAMPLES 9 TO 12

Following the same procedures and apparatus as in Example 8, the production test of N,N'-diphenyl urea was performed. The obtained results are summarized in Table 1 below.

Nitrobenzene was not detected in the filtered solution but 0.31 g of N,N'-diphenyl urea was contained therein.

The yield of the singly separated N,N'-diphenyl urea was 85%. If N,N'-diphenyl urea contained in the solution was included, a total yield was 93%. A turn over rate of the catalyst was 109 (mol-PhNo$_2$/mol-Ru.hr).

Following the same procedures as in Example 8, 3.00 g of N,N'-diphenyl urea crystals were reacted with 50.00 g of methyl alcohol. After the reaction, the reaction mixture was analyzed to obtain a 93% yield for N-phenylethyl carbamate and a 94% yield for aniline.

COMPARATIVE EXAMPLE 1

6.12 g of nitrobenzene, 37.00 g of methanol, and 0.11 g of Ru$_3$(CO)$_{12}$ were filled in an electromagnetic stirring type autoclave having an inner volume of 200 ml. Carbon monoxide was supplied to the autoclave at a pressure of 50 kg/cm$^2$ so as to obtain a CO atmosphere. The starting materials were stirred and reacted at a temperature of 160° C. for five hours. After the reaction, the solution was analyzed by liquid cromatography and found to have a nitrobenzene conversion rate of 32%. The conversion rate of N-phenylmethyl carbamate was as low as 13%, and the conversion rate of by-produced aniline was 40%. In other words, the yield

TABLE 1

| Example | Starting Material | | | Reaction Temperature (°C.) | Reaction Time (hr) | Reaction Pressure (kg/cm$^2$) |
|---|---|---|---|---|---|---|
| | Nitrobenzene (g) | Aniline (ml) | Ru$_3$(CO)$_{12}$ (g) | | | |
| 9 | 7.41 | 40.0 | 0.0202 | 180 | 1.5 | 50 |
| 10 | 3.73 | 40.0 | 0.0500 | 160 | 2.0 | 30 |
| 11 | 2.49 | 40.0 | 0.1000 | 160 | 2.0 | 10 |
| 12 | 2.45 | 40.0 | 0.1000 | 140 | 2.0 | 50 |

| Example | Solution After Reaction | | N,N'—diphenyl Urea Crystal (g) | Nitrobenzene Conversion Rate (%) | N,N'—diphenyl Urea Selectivity Coefficient (%) | Turn Over Rate (mol-PhNO$_2$/ mol-Ru · hr) |
|---|---|---|---|---|---|---|
| | Nitrobenzene (g) | N,N'—diphenyl Urea (g) | | | | |
| 9 | 1.87 | 0.35 | 8.67 | 75 | 94 | 316 |
| 10 | 0 | 0.40 | 5.18 | 100 | 87 | ≧65 |
| 11 | 0 | 0.36 | 3.05 | 100 | 80 | ≧22 |
| 12 | 0 | 0.41 | 3.49 | 100 | 93 | ≧21 |

EXAMPLE 13

The same procedures as in Example 8 were followed except that the starting materials were 1.08 g of nitrobenzene, 40.0 ml of aniline, and 0.0800 g of Ru(acac)$_3$, the reaction temperature was 160° C., 50 kg/cm$^2$ of CO were supplied, and the reaction time was 2.0 hours. As a result, 2.80 g of crystals were obtained. Nitrobenzene was not detected in the filtered solution but 0.27 g of N,N'-diphenyl urea was contained therein.

The yield of the singly separated N,N'-diphenyl urea was 90%. If N,N'-diphenyl urea contained in the solution was included, a total yield was 99%. A turn over rate of the catalyst was 36 (mol-PhNo$_2$/mol-Ru.hr).

Following the same procedures as in Example 8, a total amount of N,N'-diphenyl urea crystal was reacted with 50.00 g of ethyl alcohol. After the reaction, the reaction mixture was analyzed to obtain a 93% yield for N-phenylethyl carbamate and a 95% yield for aniline.

EXAMPLE 16

The same procedures as in Example 8 were followed except that the starting materials were 2.32 g of nitrobenzene, 40.0 ml of aniline, and 0.0817 g of Ru(-CO)$_3$(PPh$_3$)$_2$, the reaction temperature was 160° C., 50 kg/cm$^2$ of CO were supplied, and the reaction time was 1.5 hours. As a result, 3.38 g of crystals were obtained.

of N-phenylmethyl carbamate was 4%, and the yield of aniline was 13%.

COMPARATIVE EXAMPLE 2

4.63 g of aniline, 6.12 g of nitrobenzene, 37.00 g of methanol, and 0.11 g of Ru$_3$(CO)$_{12}$ were filled in an electromagnetic stirring type autoclave having an inner volume of 200 ml. Carbon monoxide was supplied to the autoclave at a pressure of 50 kg/cm$^2$ so as to obtain a CO atmosphere. The starting materials were stirred and reacted at a temperature of 160° C. for five hours. After the reaction, the solution was analyzed by liquid cromatography and found to have a 61% yield for N-phenylmethyl carbamate and a 4% yield for N,N'-diphenyl urea.

The resultant solution was placed in a −5° C. refrigerator for 24 hours, but no crystals were precipitated.

COMPARATIVE EXAMPLE 3

3.82 g of nitrobenzene, 2.85 g of aniline, 34.58 g of toluene, and 0.10 g of Ru$_3$(CO)$_{12}$ were filled in an electromagnetic stirring type autoclave having an inner volume of 200 ml. Carbon monoxide was filled at a pressure of 50 kg/cm$^2$ to obtain a CO atmosphere in the autoclave. The starting materials were stirred and reacted at a temperature of 160° C. for six hours. After the reaction, the solution was cooled to room temperature, and the reacted solution after the autoclave was evacuated was filtered to obtain 5.91 g of N,N'-diphenyl urea. The filtered solution was analyzed by liquid chromatography. No nitrobenzene was detected. The yield of the singly separated N,N'-diphenyl urea was 90%, and a turn over rate of the catalyst was 11 (mol-PhNO$_2$/mol-Ru.hr).

3.00 g of the resultant crystals and 50.00 g of methyl alcohol were filled in another electromagnetic stirring type autoclave having an inner volume of 200 ml. The starting materials were stirred and reacted at a temperature of 160° C. for three hours. After the reaction, the reaction mixture solution was analyzed and found to have a 94% yield for N-phenylmethyl carbamate and a 95% yield for aniline.

What is claimed is:

1. A method of manufacturing aromatic urethane, comprising:

the urea producing step of reacting an aromatic mononitro-compound, an aromatic primary amine, and carbon monoxide by using a catalyst having a platinum group metal-containing compound as a major constituent to prepare N,N'-di-substituted urea and of separating and recovering the resultant N,N'-di-substituted urea from a reaction solution;

the step of reacting the N,N'-di-substituted urea as an intermediate product prepared in the urea producing step with an organic compound containing a hydroxyl group to prepare an aromatic primary amine and aromatic urethane, and of separating the aromatic primary amine from the aromatic urethane, thereby obtaining the aromatic urethane; and the step of recirculating the separated aromatic primary amine in the urea producing step.

2. A method according to claim 1, wherein the platinum group metal-containing compound is a rhodium complex compound.

3. A method according to claim 1, wherein the platinum group metal-containing compound is a ruthenium complex compound.

4. A method according to claim 1, wherein the N,N'-di-substituted urea reacts with the hydroxyl group-containing organic compound without using a catalyst.

5. A method according to claim 1, wherein the aromatic primary amine is added in an excessive amount so as to use the aromatic primary amine as a solvent.

6. A method of manufacturing ureas by reacting an aromatic primary amine, an aromatic nitro-compound, and carbon monoxide by using a catalyst essentially consisting of a platinum group metal-containing compound.

7. A method according to claim 6, wherein the platinum group metal-containing compound is a rhodium complex compound.

8. A method according to claim 6, wherein the platinum group metal-containing compound is a ruthenium complex compound.

9. A method according to claim 6, wherein the aromatic primary amine is used in an excessive amount to use the aromatic primary amine as a solvent.

* * * * *

Notice of Adverse Decisions in Interference

In Interference No. 101,994, involving Patent No. 4,678,856, T. Ikariya, M. Itagaki, M. Mizuguchi, I. Sakai, O. Tajima, METHOD OF MANUFACTURING AROMATIC URETHANE AND INTERMEDIATE PRODUCT THEREOF, final judgment adverse to the patentees was rendered Jan. 22, 1991, as to claims 1-9.

*(Official Gazette August 27, 1991)*